United States Patent [19]

Gopalsami et al.

[11] Patent Number: 5,020,920
[45] Date of Patent: Jun. 4, 1991

[54] METHOD AND APPARATUS FOR MILLIMETER-WAVE DETECTION OF THERMAL WAVES FOR MATERIALS EVALUATION

[75] Inventors: Nachappa Gopalsami, Naperville; Apostolos C. Raptis, Downers Grove, both of Ill.

[73] Assignee: The United States of America as represented by the United States Department of Energy, Washington, D.C.

[21] Appl. No.: 431,363

[22] Filed: Nov. 3, 1989

[51] Int. Cl.⁵ .................... G01N 25/00; G01N 25/72
[52] U.S. Cl. ........................ 374/57; 342/53; 374/45; 374/4; 343/703; 324/630; 324/642
[58] Field of Search ............... 374/45, 122, 124, 127, 374/57, 4; 324/639, 630, 631, 632, 642; 342/351, 179, 53; 343/703

[56] References Cited

U.S. PATENT DOCUMENTS

| | | | |
|---|---|---|---|
| 3,466,654 | 9/1969 | Abronson | 374/122 |
| 4,346,716 | 8/1982 | Carr | 128/804 |
| 4,407,292 | 10/1983 | Edrich | 374/122 |
| 4,468,136 | 8/1984 | Murphy et al. | 374/17 |
| 4,499,470 | 2/1985 | Stacey | 374/122 |
| 4,557,272 | 12/1985 | Carr | 128/804 |
| 4,578,584 | 3/1986 | Baumann et al. | 250/341 |
| 4,579,463 | 4/1986 | Rosencwaig et al. | 374/17 |
| 4,707,652 | 11/1987 | Lowitz | 324/632 |
| 4,798,215 | 1/1989 | Turner | 128/736 |
| 4,874,251 | 10/1989 | Thomas et al. | 374/128 |

OTHER PUBLICATIONS

Billeter, R. T., "Using Microwave Techniques for High Temperature Measurement," Instruments and Control Systems, vol. 45, No. 2 (Feb. 1972).

Primary Examiner—William A. Cuchlinski, Jr.
Assistant Examiner—Diego F. F. Gutierrez
Attorney, Agent, or Firm—Helen S. Cordell; John M. Albrecht; William R. Moser

[57] ABSTRACT

A method and apparatus for generating thermal waves in a sample and for measuring thermal inhomogeneities at subsurface levels using millimeter-wave radiometry. An intensity modulated heating source is oriented toward a narrow spot on the surface of a material sample and thermal radiation in a narrow volume of material around the spot is monitored using a millimeter-wave radiometer; the radiometer scans the sample point-by-point and a computer stores and displays in-phase and quadrature phase components of thermal radiations for each point on the scan. Alternatively, an intensity modulated heating source is oriented toward a relatively large surface area in a material sample and variations in thermal radiation within the full field of an antenna array are obtained using an aperture synthesis radiometer technique.

10 Claims, 2 Drawing Sheets

METHOD AND APPARATUS FOR MILLIMETER-WAVE DETECTION OF THERMAL WAVES FOR MATERIALS EVALUATION

CONTRACTUAL ORIGIN OF THE INVENTION

The United States Government has rights in this invention pursuant to Contract No. W-31-109-ENG-38 between the U.S. Department of Energy and the University of Chicago.

BACKGROUND OF THE INVENTION

This invention relates to a method and apparatus for non-destructive materials testing using millimeter-wave detection of thermal waves, and more particularly, to a method and apparatus for generating thermal waves in electrically nonconducting materials and for identifying thermal inhomogeneities (including physical defects) at subsurface levels using millimeter-wave radiometry.

It is well known in the prior art that periodic heating of a sample using a beam emanating from an intensity modulated source such as a laser will generate thermal waves. Thermal waves will propagate from the heated spot, and will interact with thermal boundaries and barriers in a manner that is mathematically equivalent to the scattering and reflection of conventional propagating waves. Features on or beneath the surface of the sample that have thermal characteristics different from their surroundings will reflect and scatter thermal waves so that variations in thermal characteristics will be revealed by imaging of the thermal waves.

Variations in thermal characteristics such as density, specific heat, and, most important, thermal conductivity, arise from variations in the local lattice structure of the material, and may not be detectable with conventional optical or acoustic probes. Other features affecting thermal waves may result from changes in basic material composition or the presence of mechanical defects, such as cracks, voids, or delaminations. Many of these features can be imaged by optical, x-ray, or acoustic probes, but thermal-wave imaging may offer advantages.

Detection and imaging of thermal waves is currently accomplished by several different techniques through the effect of the thermal waves on the temperature on the surface of the sample using gas cell, optical beam deflection, or infrared radiation emitted from the sample, or through their generation of thermoelastic signals in the bulk of the sample using piezoelectric techniques. (See further, A. Rosencwaig, "Thermal-Wave Imaging," *Science*, Vol. 218, pp. 223–228, 1982, and U.S. Pat. No. 4,578,584 issued Mar. 25, 1986, to Baumann, et al.)

Difficulties in the imaging of thermal waves arise primarily from the fact that thermal waves are heavily damped and generally can travel only one or two wavelengths before becoming too weak to detect. Imaging is especially difficult in poor thermal conductors such as most ceramics where typical thermal diffusion lengths are only about 0.2 mm at a modulation frequency of 1 Hz, which compares to a diffusion length in a good thermal conductor like aluminum of 5.6 mm at 1 Hz. Therefore, defects below the surface of a thick, nonconducting sample are mostly inaccessible to prior art thermal wave imaging techniques which measure surface characteristics such as temperature.

Some prior art methods are limited in their application as well because they require physical contact between the detector and the sample (as in, for example, the use of gas-microphone or piezoelectric techniques). Detection methods involving low signal to noise ratios, or focusing on very narrow beam spots, require long integration and scanning times. Also, techniques involving infrared detection of radiation are subject to variations due to surface emissivity caused, for example, by surface irregularities, especially roughness.

It is well known in the prior art that microwave or millimeter-wave radiometry may be used to map thermal radiation and the application of microwave radiometry to medical diagnosis has provided evidence that microwave radiation at optimal wavelengths can penetrate subsurface to provide subsurface spatial resolution and to detect changes of temperature with good sensitivity. (See further, Barrett et al, "Detection of breast cancer by microwave radiometry," *Radio Science*, Vol. 12, pp. 167–171, 1977.) The present invention departs from the prior art in providing a method and apparatus for both the generation of thermal waves as well as the detection and imaging of thermal waves and the thermal features they reveal. In this sense, it is an active radiometric technique.

The use of millimeter-wave radiometry for materials testing offers several advantages. Because the millimeter waves can travel through electrically nonconducting materials without much attenuation, the radiations emitted by the entire thermal-wave swept volume of material can be detected, thus enabling deep subsurface features to be imaged. The sensitivity or minimum detectable temperature of a radiometer depends on various factors including the background antenna noise, receiver noise figure, predetection bandwidth, and post-detection integration time. With modern millimeter-wave components, sensitivities on the order of a milli-Kelvin are possible, and can be further improved by using cryogenic receivers and/or using the latest high-temperature superconducting technology for waveguide and receiver components. High signal-to-noise ratio and spatial discrimination are possible by using a focusing lens in front of an antenna horn, or by employing a dual radiometer as a phase-switched interferometer, or by changing the antenna inclination and receiving the millimeter-wave radiation at different angles. The radiometer itself is a compact system since its components including the antenna are small in the millimeter-wave range.

It is therefore a primary object of this invention to provide a method and apparatus for generating thermal waves in a sample and for measuring thermal inhomogeneities at subsurface levels using millimeter-wave radiometry.

In the accomplishment of the foregoing object, it is another important object of this invention to provide a method for measuring thermal waves which is only minimally dependent on surface emissivity.

It is another important object of this invention to provide a method for measuring thermal waves which provides a high degree of subsurface imaging capability and spatial resolution.

It is a further object of this invention to provide a full-field thermal wave imaging system which expedites the imaging process by eliminating the need to scan the object with a point-by-point technique.

It is a further object of this invention to present a system for thermal wave characterization of materials which is entirely noncontacting.

It is a further object of this invention to present an apparatus for measuring thermal waves which is compact and easy to use.

Additional objects, advantages and novel features of the invention will become apparent to those skilled in the art upon examination of the following and by practice of the invention.

SUMMARY OF THE INVENTION

To achieve the foregoing and other objects, this invention comprises a method and apparatus for orienting an intensity modulated heating source toward a narrow spot on the surface of a material sample and monitoring the temperature variation in a narrow volume of material around the spot using a millimeter-wave radiometer.

In an alternate embodiment, the invention comprises a method and apparatus for orienting an intensity modulated heating source toward a relatively large surface area in a material sample and for obtaining the spatial temperature distribution of the heated sample using an aperture synthesis radiometer technique.

BRIEF DESCRIPTION OF THE DRAWINGS

The present invention is illustrated in the accompanying drawings where:

FIG. 2 is an expanded block diagram of a Dicke-type radiometer, for use in the thermal wave point-by-point scanning system.

FIG. 3 is an expanded block diagram of a phase-switched radiometer, used in an alternate embodiment of the thermal wave point-by-point scanning system.

DETAILED DESCRIPTION OF THE INVENTION

Thermal waves may be generated in an object by any intensity modulated source, including lasers, x-rays, gamma rays, or particle beams of, for example, electrons, protons, or neutrons. Laser sources are generally selected because of easy alignment and focusing.

Figure 1:
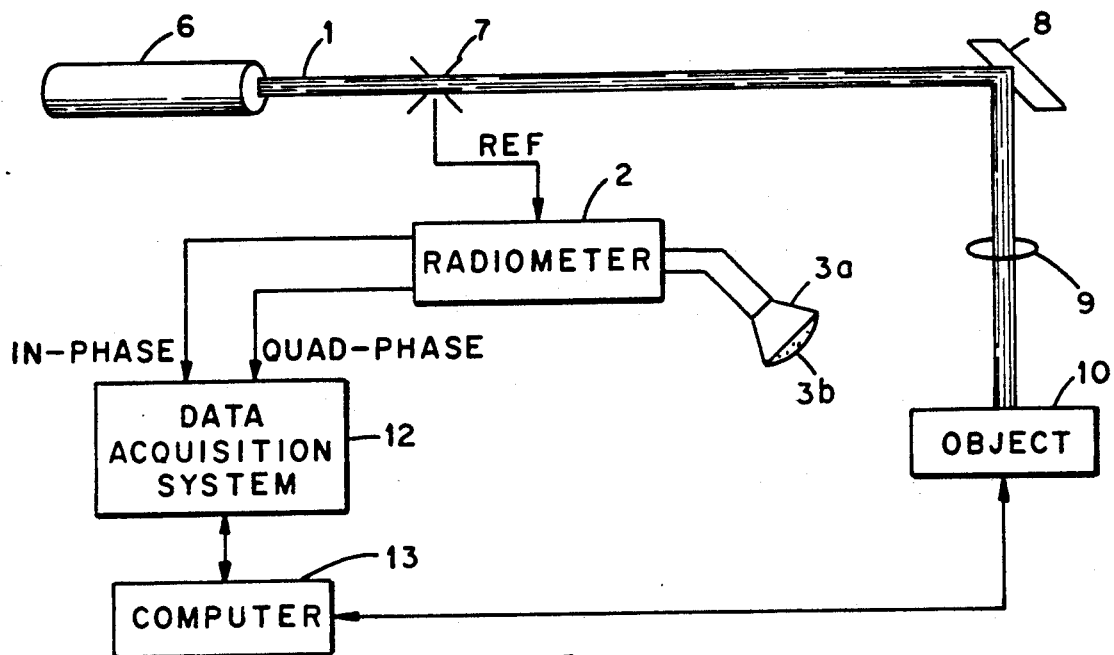
FIG. 1 is a schematic of a point-by-point scanning thermal-wave imaging system, which employs either the Dicke-type radiometer of FIG. 2 or the phase-switched radiometer of FIG. 3.

In FIG. 1, a laser 6, typically a 4-W Argon-ion type, emits a coherent beam 1. Laser 6 provides a continuous output beam 1 which must be periodically interrupted or modulated. Therefore output beam 1 from laser 6 is passed through a mechanical chopper or modulator 7, typically a toothed-wheel type, which turns beam 1 on and off at a certain frequency depending on the speed of the wheel and the number of teeth.

Using mirror 8, pulsed beam 1 is then directed to the surface of object 10 under test and lens 9, a microscope objective, focuses pulsed beam 1 to a narrow spot on the surface of object 10. Narrowing or broadening the spot on the surface to which the pulsed beam 1 is focused will narrow or broaden the subsurface volume which is swept by the resulting thermal wave.

Millimeter-wave radiometer 2, which is described in detail below, monitors the thermal emissions from the material contained in the thermal wave swept volume. Detection sensitivity and signal-to-noise ratio are improved by using a dielectric focusing lens 3b at the aperture of antenna horn 3a. Lens 3b may be focused at a plane within the thermal wave swept volume, either on the surface or below the surface of object 10, thereby narrowing the focus of detection and receiving thermal waves around locations of interest within the material.

Computer 13 moves the object 10 in a raster pattern, permitting radiometer 2 to scan object 10 point-by-point within the imaging coordinates of interest, and stores and displays amplitude and phase values of in-phase and quadrature-phase components of the signal for each point on the scan using data acquisition system 12.

The radiometer depicted in FIG. 2 is a Dicke-type radiometer, measuring temperature of an object through detection of radiation power within a given bandwidth. Thermal radiations received by antenna horn 3a within the specified bandwidth are converted by mixer 14 driven by a local oscillator 15 to an intermediate frequency (IF). The IF signal may be amplified by IF amplifier 16. A square-law detector 17 provides a slowly varying output proportional to the power of the signal at its input. A video amplifier 18 further amplifies the signal, reducing noise fluctuations at the same time.

In a Dicke-type radiometer known in the prior art, the signal at the output of video amplifier 18 would have been modulated by switching the radiometer between antenna 3a and a constant temperature source at a certain rate and will then be synchronously demodulated using the switching pulses. In a novel variation of the conventional Dicke-type configuration, the signal has been modulated by chopper 7 and is then synchronously demodulated by multiplier 19 and integrator 21 using the chopper signal 11, minimizing amplifier gain fluctuations in the in-phase component displayed or measured at measuring device 22.

In a further variation of the conventional Dicke-type configuration of the prior art, the signal proceeding through multiplier 23 is demodulated using a 90° phase shifter 20 in the reference path from chopper signal 11, providing through integrator 24 the quadrature-phase component displayed or measured at measuring device 25. Using this arrangement both the in-phase and quadrature-phase components of the thermal-wave signal are obtained with reference to the intensity modulated heating beam. This variation also minimizes the effect of amplifier fluctuations without reference to the signal of a known temperature source required in the conventional arrangement.

Given both the in-phase component and the quadrature-phase component, computer 13 in FIG. 1 may display images corresponding to both amplitude and phase values. Detection sensitivity can be enhanced by changing the antenna inclination and thus receiving the millimeter-wave radiation at different angles of view.

An alternate embodiment of the point-by-point thermal wave imaging system of the present invention uses a dual radiometer depicted in FIG. 3 which is a phase-switched interferometer or correlator. Two antenna horns 30a and 30b are of the field type and are used without focusing lenses. Horns 30a and 30b are oriented so that their field patterns overlap within the object (not shown), the overlapped portion defining a narrow volume within the thermal wave swept volume below the object's surface.

The signal derived from antenna horn 30a is converted by a mixer 31 driven by a local oscillator 32 to an IF signal which is amplified by an IF amplifier 33. The output of IF amplifier 33 is sent to both phase switch 34 and phase switch 38. Phase switch 34 reverses (180° phase shift) the phase of the signal at the rate of the chopper frequency using reference signal 11, and the signal proceeds after correlation with the signal from antenna horn 30b using broad band multiplier 35 and integrator 36 providing an in-phase component at measuring device 37. Phase switch 38 reverses the phase of the signal depending on the sense (+ or −) of the pulse in the reference path which uses a 90° phase shifter 20 on chopper signal 11, and the signal proceeds after correlation with the signal from antenna horn 30b using broad band multiplier 39 and integrator 40 to provide a quadrature-phase component at measuring device 41.

The outputs of the correlator as measured by the in-phase device 37 and quadrature-phase device 41 are proportional to the temperature in the region where the beam patterns of the antennas overlap. The volume of the overlap region may be enlarged or reduced to correspond with the thermal wave swept volume or with a more limited volume of interest. Consequently, this embodiment provides high spatial discrimination without the use of a focusing lens.

Figure 4:
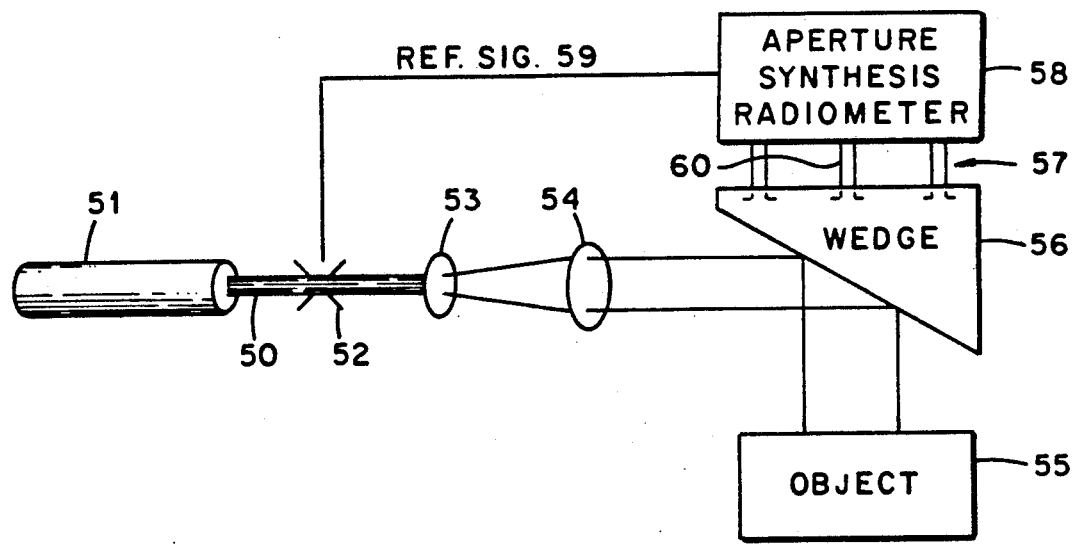
FIG. 4 is a schematic of a full-field thermal-wave imaging system, which uses a parallel processing approach to provide improved imaging speed.

An alternate embodiment of the present invention is depicted in FIG. 4, showing a full-field thermal wave imaging system.

In FIG. 4, laser beam 50 from laser 51 is passed through chopper 52 and expanded and collimated by means of lenses 53 and 54. The enlarged beam is then directed perpendicular to the surface of object 55 by a light-reflecting wedge 56 which is transparent to millimeter waves. An array of small dipole antennas 57, each of whose primary beam extends over the image area, is placed above or buried into the wedge as in striplines. As described below, the signal from central antenna 60 is cross-correlated with the signal from each antenna in array 57.

Temperature changes in the entire area under the antenna array 57 may be imaged using an aperture synthesis technique. (See further, Haslam et al., "Aperture Synthesis Thermography—A New Approach to Passive Microwave Temperature Measurements in the Body," *IEEE Transactions on Microwave Theory and Techniques*, vol. MTT-32, pp. 829–839, 1984.) Aperture synthesis radiometer 58 correlates signals of each antenna in array 57 with the central antenna signal using reference signal 59 from chopper 52 for phase switching. Radiometer 58 includes a phase-switched interferometer of the type depicted in FIG. 3 for each pair of signals to be correlated along with software or hardware for Fourier transformation. Performing Fourier transformation of in-phase and quadrature-phase components will yield temperature distribution data for that portion of the object within the primary beam of each antenna.

Using the embodiment depicted in FIG. 4, each antenna in array 57 must have as its field of view the entire imaging area which determines the size of the imaging area. The maximum angular resolution is given by the ratio of the observing wavelength over the distance separating the far-end antennas. The depth of observation volume within the material is determined by the penetration of the thermal radiation sampled. Using higher frequencies will improve spatial resolution but decrease penetration. Use of the embodiment depicted in FIG. 4 provides a parallel processing approach without the need for time consuming point-by-point scanning.

The foregoing description of a preferred embodiment of the invention has been presented for purposes of illustration and description. It is not intended to be exhaustive or to limit the invention to the precise form disclosed, and obviously many modifications and variations are possible in light of the above teaching. The embodiments described explain the principles of the invention and practical applications and should enable others skilled in the art to utilize the invention in various embodiments and with various modifications as are suited to the particular use contemplated. It is intended that the scope of the invention be defined by the claims appended hereto.

The embodiments of this invention in which an exclusive property of privilege is claimed are defined as follows:

1. An apparatus for identifying thermal inhomogeneities in electrically nonconducting materials comprising:
   an intensity modulated heat source directed toward a material sample, generating thermal waves in said sample,
   antenna means directed toward said sample, for receiving thermal radiation resulting from said thermal waves within said sample,
   radiometer means for monitoring said thermal radiation, and for synchronously demodulating said thermal radiation with respect to the modulating signal of said intensity modulated heat source, and
   imaging means for displaying in-phase and quadrature-phase components of said thermal radiation, revealing variations in said thermal radiation caused by thermal inhogeneities in said sample.

2. An apparatus for identifying thermal inhomogeneities in electrically nonconducting materials comprising:
   an intensity modulated heat source directed toward a material sample, generating thermal waves in said sample,
   antenna means directed toward said sample, for receiving thermal radiation resulting from said thermal waves within said sample,
   radiometer means for receiving and displaying a signal in the millimeter-wave frequency from said antenna means, said signal reflective of said thermal radiation which reveals variations in said thermal radiation caused by thermal inhomogeneities in said sample, and,
   said radiometer means including means for synchronously demodulating said signal into in-phase and quadrature-phase components with respect to the modulating signal of said intensity modulated heat source.

3. The apparatus of claim 2 wherein said antenna means comprises an array of dipole antennas each of whose primary beam extends over the image area providing means for aperture synthesis.

4. The apparatus of claim 3 further comprising means for correlating the signal from each antenna in said array with the signal from the central antenna and demodulating the cross-correlated signal with respect to the modulating signal of said intensity modulated heat source.

5. The apparatus of claim 2 wherein said radiometer means includes a Dicke-type radiometer which is modulated with reference to said intensity modulated heat source.

6. The apparatus of claim 5 wherein said Dicke-type radiometer is demodulated with respect to an intensity modulated beam which has been shifted 90 degrees out of phase.

7. The apparatus of claim 2 wherein said antenna means comprises at least two field type antennas with overlapping field volumes.

8. A method for identifying thermal inhomogeneities at subsurface levels comprising the steps of:
generating thermal radiations in an object using an intensity modulated source,
detecting said thermal radiations from a volume within said object and using radiometer means for converting said thermal radiations into a millimeter-wave signal,
synchronously demodulating said millimeter-wave signal into in-phase and quadrature-phase components with respect to the modulating signal of said intensity modulated source, and
storing and displaying amplitude and phase values of said in-phase and quadrature-phase components of said signal, thereby revealing variations in said thermal radiation caused by thermal inhomogeneities in said object.

9. The method of claim 8 wherein detecting said thermal radiations includes employing an array of dipole antennas and directing each of said antennas toward said object, and pairing each of said antennas with a central antenna and correlating millimeter-wave signals corresponding to thermal radiations derived from said object to provide aperture sampling in the plane of said antenna array.

10. The method of claim 9 wherein storing and displaying amplitude and phase values of said in-phase and quadrature-phase components of said signal includes performing Fourier transformation of said in-phase and quadrature-phase values to provide temperature distribution of said object within the field of view of said antenna array.

* * * * *

UNITED STATES PATENT AND TRADEMARK OFFICE
CERTIFICATE OF CORRECTION

PATENT NO. : 5,020,920

DATED : June 4, 1991

INVENTOR(S) : Nachappa Gopalsami et al.

It is certified that error appears in the above-indentified patent and that said Letters Patent is hereby corrected as shown below:

The Drawing Sheet, consisting of Figs. 2 & 3, should be added as shown on the attached page.

Signed and Sealed this

Eighth Day of February, 1994

Attest:

BRUCE LEHMAN

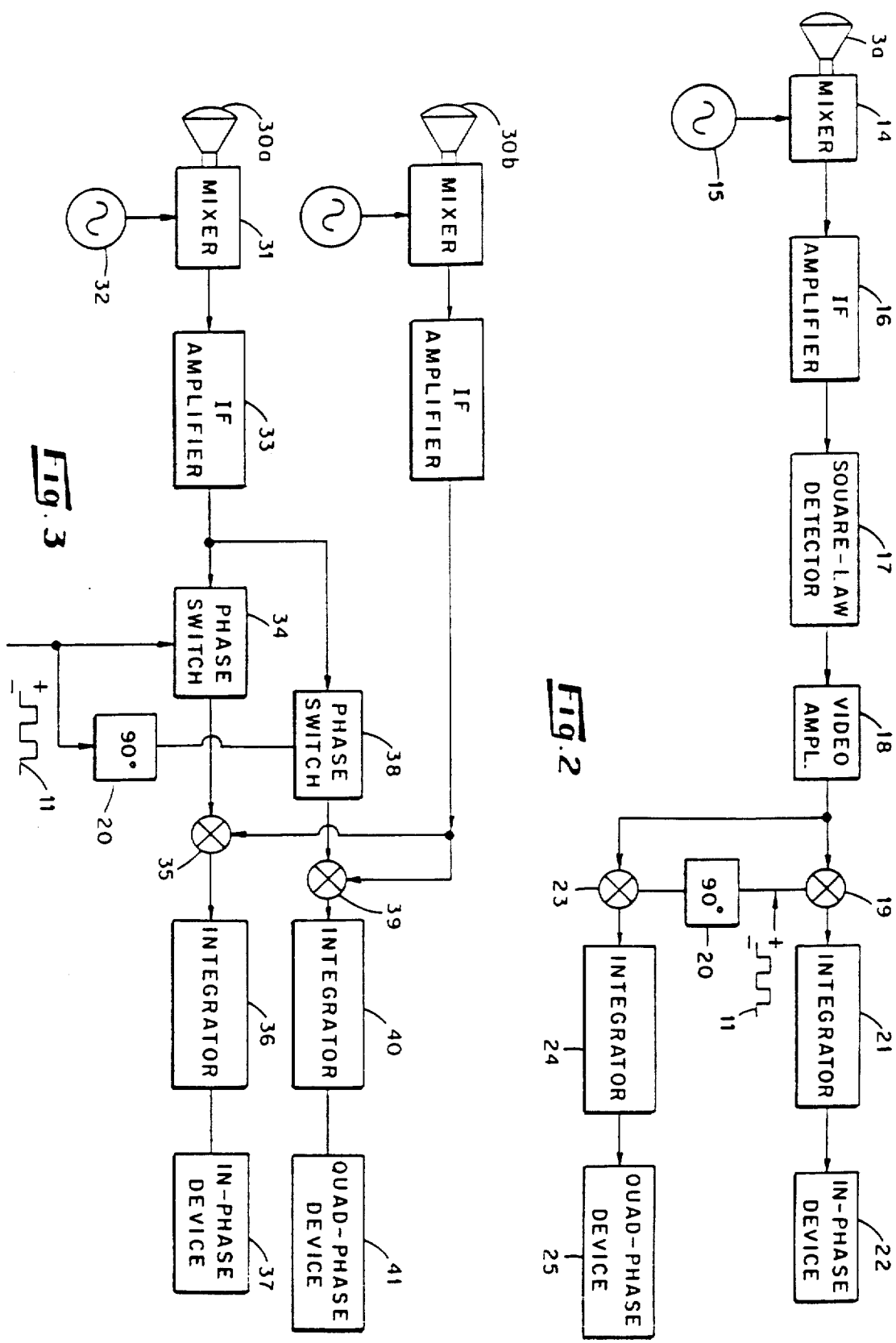

Attesting Officer    Commissioner of Patents and Trademarks